United States Patent
Maliszewskyj et al.

(10) Patent No.: US 6,723,877 B1
(45) Date of Patent: Apr. 20, 2004

(54) DIMETHYLFORMAMIDE SYNTHESIS VIA REACTIVE DISTILLATION OF METHYL FORMATE AND DIMETHYLAMINE

(75) Inventors: Robin Joyce Maliszewskyj, Middletown, MD (US); Michael Gerard Turcotte, Bethlehem, PA (US); John William Mitchell, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/462,916

(22) Filed: Jun. 16, 2003

(51) Int. Cl.$^7$ .............................................. C07C 233/00
(52) U.S. Cl. ...................... 564/215; 564/216
(58) Field of Search .................. 524/215, 216

(56) References Cited

U.S. PATENT DOCUMENTS

| | | | |
|---|---|---|---|
| 2,866,822 A | 12/1958 | Siefen et al. ................ | 260/561 |
| 3,072,725 A | 1/1963 | Surman ...................... | 260/561 |
| 3,530,182 A | 9/1970 | Haynes et al. .............. | 260/561 |
| 4,098,820 A | 7/1978 | Couteau et al. ............. | 260/561 |
| 4,853,485 A | 8/1989 | Bellis ......................... | 564/215 |

FOREIGN PATENT DOCUMENTS

| | | | |
|---|---|---|---|
| RO | 75982 | 2/1981 | ................. 103/30 |

Primary Examiner—Johann Richter
Assistant Examiner—Sikarl A. Witherspoon
(74) Attorney, Agent, or Firm—Mary E. Bongiorno

(57) ABSTRACT

A continuous process for the production of dimethylformamide comprising the steps:

(a) reacting methyl formate and dimethylamine in a reactive distillation column under conditions to form dimethylformamide and by-product methanol;

(b) vaporizing the by-product methanol and generating a liquid dimethylformamide while in said reactive distillation column;

(c) removing at least a major portion of the by-product methanol as an overhead from said reactive distillation column;

(d) removing a crude liquid dimethylformamide containing residual by-product methanol as a bottoms fraction from said reactive distillation column;

(e) introducing said bottoms fraction containing dimethylformamide and residual by-product methanol to a purification column wherein the by-product methanol is removed from said dimethylformamide as an overhead and purified dimethylformamide is removed as a bottoms fraction; and, optionally, (f) recycling the by-product methanol removed as an overhead from the purification column to the reactive distillation column.

13 Claims, 1 Drawing Sheet

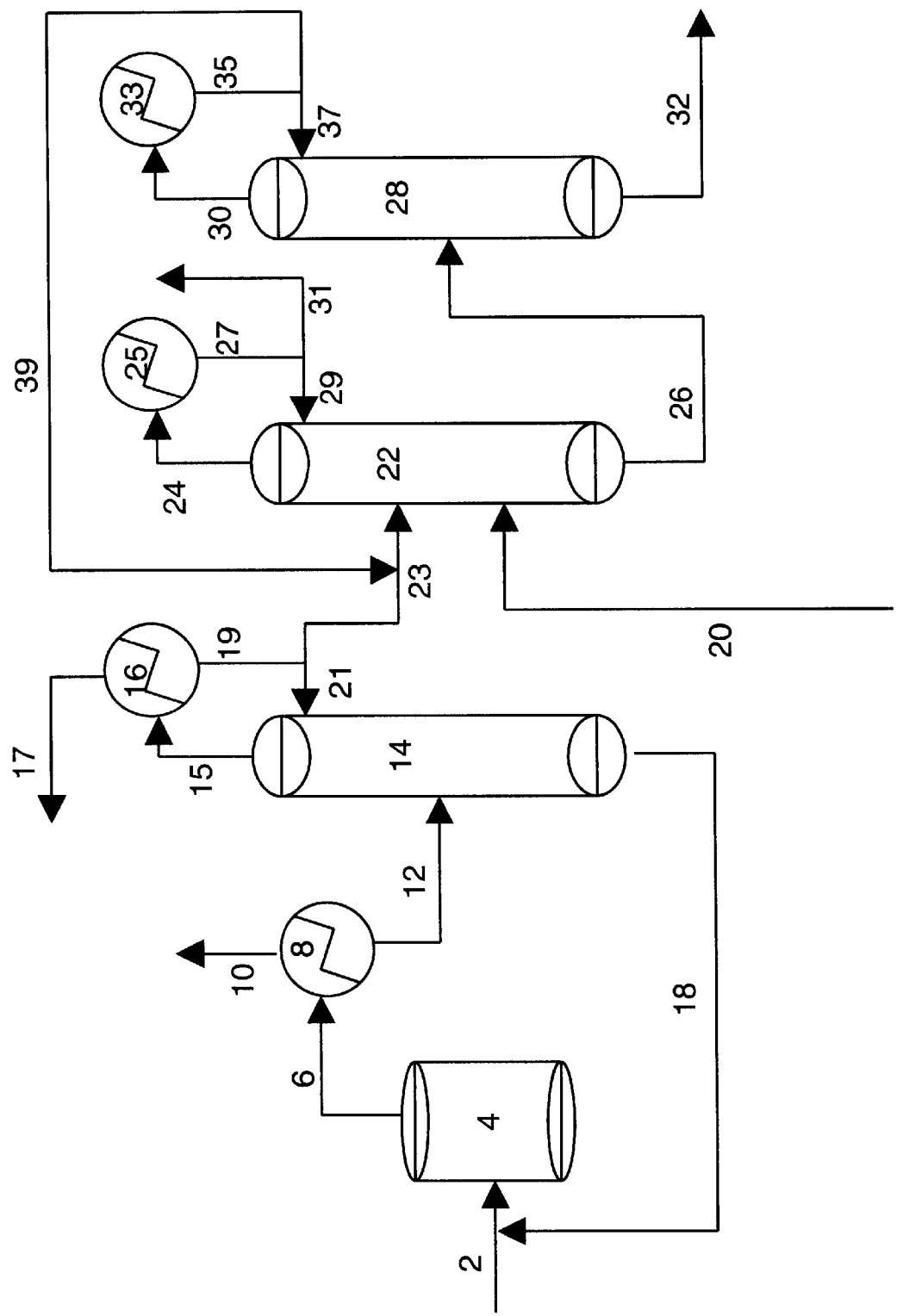

DIMETHYLFORMAMIDE SYNTHESIS VIA REACTIVE DISTILLATION OF METHYL FORMATE AND DIMETHYLAMINE

BACKGROUND OF THE INVENTION

Dimethylformamide, a widely used solvent in the chemical industry, has been prepared commercially by two processes. Current technology for the manufacture of dimethylformamide is based on the direct carbonylation of dimethylamine, i.e., the reaction of carbon monoxide with dimethylamine in the presence of a soluble catalyst. Although the process is commercial, there are difficulties with this process. These problems include: carbon monoxide production must be fairly local, since carbon monoxide is not easily transportable; a cooling system is required to control the reactor temperature because of the exothermic reaction of dimethylamine and carbon monoxide, and water, if present, can lead to catalyst decomposition and fouling of the reactor cooler through insoluble salt formation.

An alternative route to dimethylformamide, which has the added advantage of requiring no catalyst, is the batch or continuous reaction of dimethylamine with methyl formate.

The following patents illustrate various methods of preparing dimethylformamide; they are:

U.S. Pat. No. 2,866,822 (Siefen et al., 1958) discloses a process for producing formamides in a vertical reaction column. Carbon monoxide is passed through a dispersion plate at the bottom of the column and a methylamine, e.g., dimethylamine, and an alkali metal methylate catalyst in methanol solution are introduced at the top of the fractionation column. Off-gases pass from the reactor at the top of the reactor and products are withdrawn at the bottom.

U.S. Pat. No. 3,072,725 (Surman, 1963) discloses a continuous process for producing dimethylformamide wherein methyl formate and dimethylamine are reacted in a reaction zone. The reaction products are passed to a heated distillation zone (reactor-stripper) for vaporizing and effecting separation of the unreacted dimethylamine and methyl formate from the liquid products methanol and dimethylformamide. Unreacted methyl formate and dimethylamine are returned to the top of the reactor-stripper distillation column as reflux. Liquid products, e.g., all of the methanol and dimethylformamide, essentially free of methyl formate and dimethylamine, are removed from the bottom of the reactor-stripper distillation column and passed to a second distillation zone. The second distillation effects separation of water and methanol from the dimethylformamide.

U.S. Pat. No. 3,530,182 (Haynes et al., 1970) discloses a method for producing hydrocarbon formamides in an autoclave by the catalytic reaction of carbon dioxide, hydrogen, and primary or secondary amines in the presence of halogen-containing transition metal compounds. Dimethylformamide is prepared by reacting carbon dioxide, hydrogen and dimethylamine in the presence of dichloro-bis(triphenylphosphine)palladium.

U.S. Pat. No. 4,098,820 (Couteau et al., 1978) discloses a direct carbonylation process for producing dimethylformamide wherein carbon dioxide is reacted with a recycled liquid dimethylamine mixture and a methanolic solution of an alkali metal or earth metal methoxide catalyst. The recycled liquid mixture is used to draw in carbon dioxide gas and disperse the carbon dioxide gas within the reaction medium.

U.S. Pat. No. 4,853,485 (Bellis, 1989) discloses the formation of dimethylformamide at reasonable yield by the reaction of formamide and methanol in the presence of a quaternary ammonium catalyst.

RO 75982 (Serban et al., 1981) discloses a continuous process for the reaction of methanol and dimethylamine in the presence of an activated charcoal catalyst. The reaction mixture, which includes dimethylformamide, methyl formate, and methanol, are rectified by known means.

SUMMARY OF THE INVENTION

This invention relates to an improvement in a continuous process for the production of dimethylformamide. In the basic process, methyl formate and dimethylamine are reacted at a temperature and pressure sufficient to form dimethylformamide, generating by-product methanol. The improvement in the process resides in the steps:

(a) reacting methyl formate and dimethylamine in a reactive distillation column under conditions to form dimethylformamide and by-product methanol;

(b) vaporizing the by-product methanol and generating a liquid dimethylformamide while in said reactive distillation column;

(c) removing at least a major portion of the by-product methanol as an overhead from said reactive distillation column;

(d) removing a crude liquid dimethylformamide containing residual by-product methanol as a bottoms fraction from said reactive distillation column;

(e) introducing said bottoms fraction containing dimethylformamide and residual by-product methanol to a purification column wherein the by-product methanol is removed from said dimethylformamide as an overhead and purified dimethylformamide is removed as a bottoms fraction; and, optionally, (f) recycling the by-product methanol removed as an overhead from the purification column to the reactive distillation column.

There are significant advantages that can be achieved by this process and these include:

an ability to integrate reaction of dimethylamine and methyl formate and the initial separation of the resulting product and by-product in a single piece of equipment;

an ability to integrate the heat generated in the reaction process within the reaction and distillation stages of a single column; and, an ability to react methyl formate and dimethylamine in the distillation zone to produce dimethylformamide on a continuous basis without fouling of the distillation/separation stages.

BRIEF DESCRIPTION OF THE DRAWING

The drawing is a flow diagram illustrating the heat integration in a process, which includes the generation of methyl formate and its reaction with dimethylamine to form dimethylformamide.

DETAILED DESCRIPTION OF THE INVENTION

The improved process for the production of dimethylformamide described herein involves dehydrogenation of methanol to produce the intermediate reactant methyl formate and then the subsequent reaction with dimethylamine to produce dimethylformamide and by-product methanol. The overall reaction consumes methanol and dimethylamine to produce dimethylformamide and hydrogen ($H_2$). The process can be considered in two stages (a) synthesis of methyl formate and (b) synthesis of dimethylformamide. The process can be summarized by the following reactions:

Step 1

Step 2

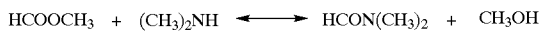

Overall

To facilitate an understanding of the invention, reference is made to the drawing. Methyl formate is formed by passing gaseous methanol via line 2 to an isothermal dehydrogenation reactor 4 operating at pressures as low as 50 psig (446 kPa) and temperatures ranging between 200° F. (93° C.) and 750° F. (399° C.), depending on the catalyst. Typical reaction conditions are in the range 500° F. (260° C.) to 550° F. (288° C.) and 100 to 125 psig (791 to 963 kPa). The methanol, when passed over a copper-based catalyst held in tubes within isothermal dehydrogenation reactor 4, generates methyl formate and hydrogen. Single-pass conversion of methanol to methyl formate is approximately 24%, with small methanol losses to carbon monoxide (1%) and methyl ether (0.01%).

The reaction products generated in isothermal dehydrogenation reactor 4 are comprised of hydrogen and methyl formate. They are removed via line 6 and cooled in condenser 8 to approximately 110° F. (44° C.). Hydrogen and residual carbon dioxide are removed as a gaseous overhead from condenser 8 via line 10 and a liquid stream comprised of methyl formate and methanol is removed from condenser 8 via line 12. Residual methyl formate present in the gas stream (line 10) from condenser 8 can be recovered by conventional means such as by contact with liquid methanol. The resultant gaseous stream obtained after contact with methanol, containing mostly hydrogen and some carbon monoxide, can be recovered for fuel or other uses.

The liquid stream in line 12, which is approximately 80% by weight unreacted methanol and 20% methyl formate, is concentrated to about 95% methyl formate in distillation column 14. Methyl formate is removed as an overhead via line 15. From there, the overhead stream is at least partially condensed in condenser 16. Any residual vapor, e.g., hydrogen and carbon monoxide, is removed via line 17. The condensate exits condenser 16 via line 19, with a portion introduced as reflux via line 21 to distillation column 14 and a remaining portion removed via line 23 and introduced as feed to reactive distillation column 22. The liquid methanol present as a bottoms fraction in distillation column 14 is removed via line 18 where, optionally it is joined with feed methanol in line 2. Thus, the unreacted methanol from distillation column 14 is recycled to the isothermal dehydrogenation reactor 4 and the energy recovered therefrom.

Liquid dimethylamine (optionally gaseous dimethylamine) is conveyed in line 20 and the liquid, concentrated methyl formate in line 23 are introduced in stoichiometric proportions to reactive distillation column 22. The reactive distillation column 22 is operated at a temperature and pressure such that not only does reaction take place between methyl formate and dimethylamine but the resulting by-product methanol is generated as a vapor and product dimethylformamide is generated as a liquid.

Differing from other prior processes, the heat of reaction generated by the reaction of methyl formate and dimethylamine is utilized to assist and maintain a temperature in reactive distillation column 22 sufficient to vaporize and drive at least a major portion, and generally at least 90% of the by-product methanol, to the top of the reactive distillation column 22. In this process, then, at least a major portion, and preferably most of the by-product methanol, is removed as an overhead via line 24. Thus, the reaction of dimethylamine and methyl formate and the separation of product from the by-product methanol are effected in a single piece of equipment.

The reaction portion of reactive distillation column 22 operates between about 220° F. (104° C.) and 250° F. (121° C.), and the reboiler is kept below 380° F. (193° C.) at a column operating pressure of approximately 10 to 85 psig (170 to 687 kPa), preferably 20 to 60 psig (239 to 515 kPa), to avoid destabilization of the dimethylformamide.

The overhead in line 24 is passed to condenser 25 where at least a portion of the overhead vapor is partially condensed. A portion of the condensate is removed from condenser 25 via line 27 and sent as reflux to reactive distillation column 22 via line 29. If all of the overhead in line 24 is condensed, the remaining portion of the condensate from condenser 25 is available for recycle to the methyl formate reactor or elsewhere by line 31. An alternative to this method is to partially condense only a portion of the overhead in line 24 and then remove the vapor by a line not shown. Typically, more than 90% of the methanol is removed via line 24 from the reactive distillation column 22. Often, the methanol is recycled for conversion to methyl formate in isothermal dehydrogenation reactor 4.

The bottoms fraction in reactive distillation column 22 contains dimethylformamide and a small amount, less than 50% and typically 10% or less, of by-product methanol with trace levels of water and methyl formate. That bottoms fraction is removed via line 26 and is purified in purification column 28. Purification column 28 is operated under conditions sufficient to generate methanol as an overhead vapor and a purified dimethylformamide as a liquid bottoms fraction. The overhead is removed via line 30 and condensed in condenser 33. The condensate is removed via line 35 and a portion is sent via line 37 as reflux to purification column 28. Another portion may be returned via line 39 and joined with line 23 for introduction to the reactive distillation column 22. If partial condensation is effected in condenser 33, the vapor can be removed by a line not shown and recycled as vapor feed to reactive distillation column 22 or used elsewhere in the process, if desired. The dimethylformamide product is removed via line 32 and sent to storage.

The following examples illustrate various embodiments of the invention and are not intended to restrict the scope thereof.

EXAMPLE 1

Reactive Distillation of Dimethylamine and Methyl Formate

Liquid dimethylamine and methyl formate are combined at 70.1 lbmol/hr each in a reactive distillation column 22 operating at 45 psig. The methyl formate feed stream and recycled methanol stream entering the reactive distillation column 22 having 57 stages contain a total of 14.2 lbmol methanol. The reflux ratio is set at 1.77, and the boil up ratio is set up at 1.8. The distillate contains 77.1 lbmol/hr methanol, as well as traces of methyl formate, dimethylamine, carbon monoxide and $H_2$. The bottom fraction contains 70.1 lbmol/hr dimethylformamide and 7.1 lbmol/hr methanol, as well as a small amount of water.

The condenser duty for this column is 3.1 MMBTU/hr, and the reboiler duty is 2.5 MMBTU/hr. The dimethylformamide bottoms stream is then fed to a second distillation column operating at 517 mmHg, a reflux ratio of 10.1 and a boil up of 0.82. The dimethylformamide is completely separated from the remaining methanol to an impurity level of less than 300 ppb. This second column has a condenser duty of 1.2 MMBTU/hr and a reboiler duty of 0.97 MMBTU/hr. Overall, yield of dimethylamine and methyl formate to dimethylformamide is 99.97%.

In a variation, 1A, the above procedure is repeated except that gaseous dimethylamine is added via line 20 as a feed to reactive distillation column 22 instead of in liquid form. The use of gaseous dimethylamine does increase condenser duty.

In another variation, 1B, the vapor stream in line 24 is partially condensed such that the amount of overhead condensed is equal to an amount consistent with the defined reflux ratio and the overhead from the condenser is removed as a vapor. Likewise, the vapor stream in line 30 is partially condensed such that the amount of overhead condensed is equal to an amount consistent with the defined reflux ratio and the overhead from the condenser is removed as a vapor and recycled for introduction to the reactive distillation column 22.

COMPARATIVE EXAMPLE 2
Methyl Formate and Dimethylamine Combined as Liquids
Traditional Reactor
No Methanol Present in Feed Stream The process in Example 1 was repeated, except that the methyl formate and dimethylamine were combined as liquids in a traditional autoclave reactor and no methanol was present in the feed stream. The cooling duty for the reactor was 1.2 MMBTU/hr. Reaction products, containing 69.86 lbmol/hr each of dimethylformamide and methanol and 0.24 lbmol/hr each of dimethylamine and methyl formate at 180° F. (82° C.) were then separated in a single distillation column operating at 517 mm Hg with a reflux ratio of 2.27 and a boil up ratio of 3.22. Condenser and reboiler duties for the column were 3.6 and 3.8 MMBTU/hr, respectively. The final dimethylformamide product contained only traces of methanol, methyl formate, and dimethylamine.

COMPARATIVE EXAMPLE 3

Direct Carbonylation of Dimethylamine With Carbon Monoxide

The traditional direct carbonylation of dimethylamine with carbon monoxide was simulated using a 25% excess of carbon monoxide in the presence of a sodium-based catalyst in a methanol solution. Products from the 250° F. (121° C.), 285 psig (2066 kPa) reaction were evaporated under vacuum and then fed to two successive vacuum distillation columns to purify the dimethylformamide. Process conditions were typical for the industry. The final product contained methanol and water at the ppb level and minor traces of dimethylamine.

Results from the Example 1, variations, and comparative examples are tabulated in the Table below. It is evident from the data in the Table that the process of the invention disclosed in Example 1 is superior in both energy usage and reagent yield to product.

TABLE

COMPARISON OF SIMULATION RESULTS FOR DIRECT CARBONYLATION OF DIMETHYLAMINE, REACTION OF DIMETHYLAMINE WITH METHYL FORMATE IN A TRADITIONAL REACTOR, AND REACTIVE DISTILLATION OF DIMETHYLAMINE AND METHYL FORMATE

| Heat Duties | Carbonylation w/CO Comp. Ex 3 | Traditional MeFO Reactor Comp. Ex 2 | Reactive Dist. w/MeFO Ex 1 | Gaseous Dimethylamine Ex 1A | Partial Condense Ex 1B |
|---|---|---|---|---|---|
| BTU/lb. DMF | | | | | |
| Reactor Cooler | 288 | 243 | | | |
| Evaporator | 253 | | | | |
| Condenser 25 | 293 | 710 | 618 | 647 | 416 |
| Reboiler 22 | 226 | 753 | 494 | 358 | 498 |
| Condenser 33 | 705 | | 243 | 243 | 218 |
| Reboiler 28 | 683 | | 189 | 189 | 189 |
| Total Duty | 2448 | 1706 | 1543 | 1633 | 1321 |
| Yield to DMF | | | | | |
| DMA Basis | 91.17% | 99.63% | 99.98% | 99.98% | 99.98% |
| MF Basis | | 99.63% | 99.97% | 99.97% | 99.97% |
| CO Basis | 72.79% | | | | |

Reboiler 22 is the reboiler for reactive distillation column 22.
Reboiler 28 is the reboiler for purification column 28.

While use of methyl formate as a reagent with dimethylamine to produce dimethylformamide is known, the above process as described in Example 1 comprises the unique integration of reaction and distillation, which efficiently utilizes the heat of reaction for assisting the separation of the by-product methanol and product dimethylformamide within the reactive distillation column. This method eliminates a reaction step requiring cooling and eliminates an energy input step in the distillation of by-product from product dimethylformamide. Furthermore, concurrent reaction and separation of the reaction products from the reaction mixture drives the equilibrium further than would be possible in a traditional reactor.

What is claimed is:

1. In a continuous process for the production of dimethylformamide which comprises reacting methyl formate and dimethylamine at a temperature and pressure sufficient to form dimethylformamide, the improvement which comprises the steps:
   (a) reacting methyl formate and dimethylamine in a reactive distillation column to form dimethylformamide and by-product methanol;
   (b) operating said reactive distillation column under conditions sufficient for vaporizing by-product methanol while generating liquid dimethylformamide;
   (c) removing a major portion of said by-product methanol as an overhead from said reactive distillation column; and,
   (d) removing a crude dimethylformamide containing a minor fraction of by-product methanol as a bottoms fraction from said reactive distillation column.

2. The process of claim 1 wherein the reactive distillation column is operated at a pressure of 10 to 85 psig (170 to 687 kPa).

3. The process of claim 1 wherein the reactive distillation column is operated at a reboiler temperature below about 193° C.

4. The process of claim 3 wherein reaction portion of the reactive distillation column is operated at a temperature of from about 104 to 121° C.

5. The process of claim 1 wherein dimethylamine is introduced to said reactive distillation column as a liquid.

6. The process of claim 1 wherein at least 90% of the by-product methanol is removed as an overhead from said reactive distillation column.

7. The process of claim 1 wherein said bottoms fraction containing dimethylformamide and by-product methanol in step (d) is introduced to a purification column wherein by-product methanol is removed as an overhead from said purification column and purified dimethylformamide is removed as a bottoms fraction.

8. In a continuous process for the production of dimethylformamide which comprises reacting methyl formate and dimethylamine at a temperature and pressure sufficient to form dimethylformamide, the improvement which comprises the steps:
   (a) dehydrogenating methanol in a dehydrogenation reactor generating methyl formate;
   (b) reacting methyl formate generated in step (a) with dimethylamine in a reactive distillation column to form dimethylformamide and by-product methanol;
   (c) operating said reactive distillation column under conditions for vaporizing the by-product methanol and for generating liquid dimethylformamide;
   (d) removing said by-product methanol as an overhead from said reactive distillation column,
   (e) removing a liquid crude dimethylformamide containing by-product methanol as a bottoms fraction from said reactive distillation column; and,
   (f) introducing said bottoms fraction containing dimethylformamide and by-product methanol to a purification column wherein by-product methanol is removed as an overhead from said purification column and purified dimethylformamide is removed as a bottoms fraction.

9. The process of claim 8 wherein the reactive distillation column is operated at a pressure of 10 to 85 psig (170 to 687 kPa).

10. The process of claim 9 wherein the reactive distillation column is operated at a reboiler temperature below about 193° C.

11. The process of claim 10 wherein reaction portion of the reactive distillation column is operated at a temperature of from 104 to 121° C.

12. The process of claim 8 wherein the methanol removed as an overhead from the purification column and is recycled to the reactive distillation column.

13. The process of claim 8 wherein the methanol removed from the reactive distillation column is recycled to the dehydrogenation reactor.

* * * * *